(12) United States Patent
Mitas et al.

(10) Patent No.: US 12,240,847 B2
(45) Date of Patent: *Mar. 4, 2025

(54) PROCESS FOR MAKING PALBOCICLIB

(71) Applicant: SYNTHON B.V., Nijmegen (NL)

(72) Inventors: Petr Mitas, Blansko (CZ); Oldrich Smekal, Blansko (CZ)

(73) Assignee: Synthon B.V., Nijmegen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/474,840

(22) Filed: Sep. 26, 2023

(65) Prior Publication Data

US 2024/0034732 A1  Feb. 1, 2024

Related U.S. Application Data

(63) Continuation of application No. 17/057,425, filed as application No. PCT/EP2019/063085 on May 21, 2019, now Pat. No. 11,858,928.

(30) Foreign Application Priority Data

May 24, 2018 (EP) .................................. 18174119

(51) Int. Cl.
C07D 471/04 (2006.01)
(52) U.S. Cl.
CPC ................. C07D 471/04 (2013.01)
(58) Field of Classification Search
CPC .................................................... C07D 471/04
USPC ......................................................... 544/279
See application file for complete search history.

(56) References Cited

FOREIGN PATENT DOCUMENTS

| WO | WO 03/062236 A1 | 7/2003 |
| WO | WO 2014/128588 A1 | 8/2014 |
| WO | WO 2016/016769 A1 | 2/2016 |
| WO | WO 2016/030439 A1 | 3/2016 |
| WO | WO 2018/065999 A1 | 4/2018 |

OTHER PUBLICATIONS

S. Duan et al., "Palbociclib Commercial Manufacturing Process Development. Part I: Control of Regioselectivity in a Grignard-Mediated $S_NAr$ Coupling" Org. Process Res. Dev., 20, pp. 1191-1202.
M. T. Maloney et al., "Palbociclib Commercial Manufacturing Process Development. Part II: Regioselective Heck Coupling with Polymorph Control for Processability" Org. Process Res. Dev., 20, No. 7, Jul. 15, 2016, pp. 1203-1216.
B. P. Chekal et al., "Palbociclib Commercial Manufacturing Process Development. Part III: Deprotection Followed by Crystallization for API Particle Property Control" Org. Process Res. Dev., 20, pp. 1217-1226.

Primary Examiner — Taofiq A Solola
(74) Attorney, Agent, or Firm — Buscher Patent PLLC

(57) ABSTRACT

The present invention relates to a process for preparation of palbociclib, compound of formula (1) or a salt thereof,

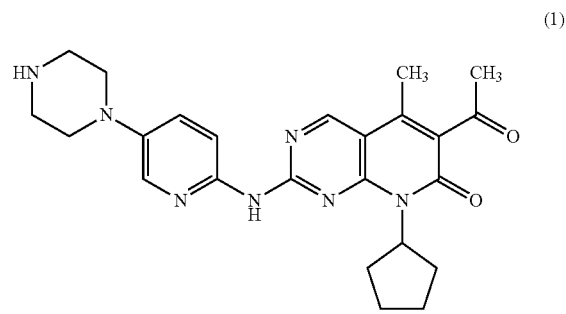

(1)

wherein an intermediate, compound (2), is formed by reacting a compound of formula (3) and a compound of formula (4) in a solvent mixture comprising methanol and butanol:

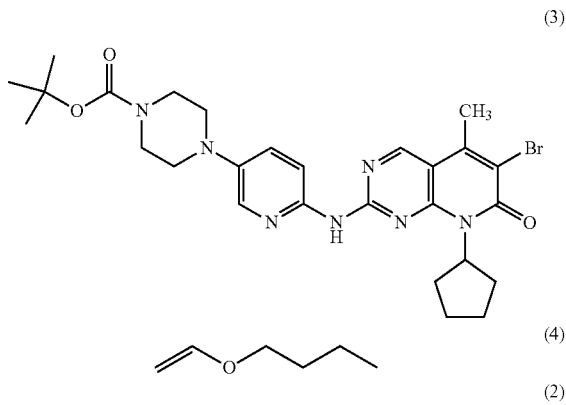

(3)

(4)

(2)

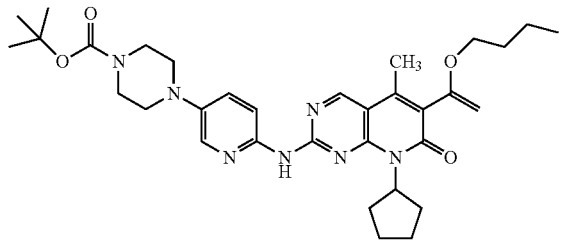

The intermediate (2) can be transformed into palbociclib or a salt thereof.

11 Claims, 1 Drawing Sheet

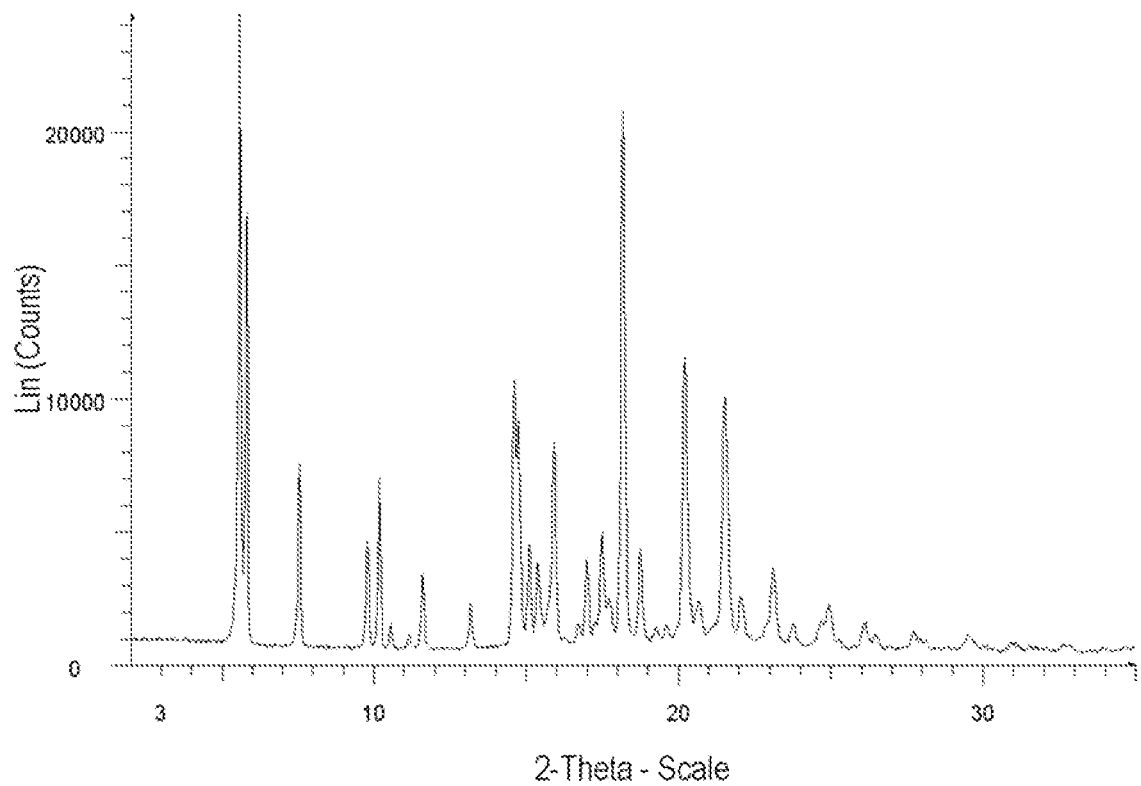

PROCESS FOR MAKING PALBOCICLIB

CROSS-REFERENCE TO RELATED APPLICATIONS

The present application is a Continuation under 35 U.S.C. § 120 of co-pending application Ser. No. 17/057,425, filed Nov. 20, 2020, the entire contents of which are incorporated herein by reference, which is a U.S. National Stage application under 35 U.S.C. § 371 of PCT/EP2019/063085, filed May 21, 2019, which claims the benefit of priority under 35 U.S.C. § 119 to European patent application no. EP 18174119.0, filed May 24, 2018.

The present invention relates to a new process for preparation of palbociclib.

BACKGROUND OF THE INVENTION

Palbociclib, chemically 6-Acetyl-8-cyclopentyl-5-methyl-2-[5-(1-piperazinyl)pyridin-2-ylamino]pyrido[2,3-d]pyrimidin-7(8H)-one of formula (I),

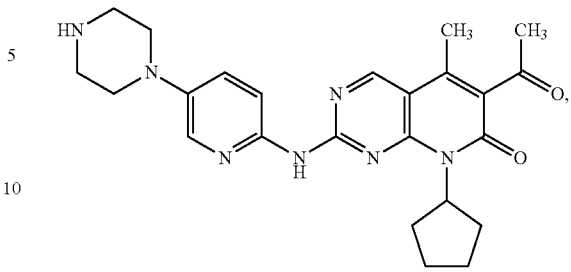

is a small-molecule inhibitor of cyclin-dependent kinase (CDK) 4 and CDK 6, which is used in combination with letrozole or fulvestrant for the treatment of postmenopausal women with estrogen receptor (ER)-positive, human epidermal growth factor receptor 2 (HER2)-negative advanced breast cancer.

Palbociclib is marketed in form of hard capsules under trade name Ibrance by Pfizer. Palbociclib was first disclosed in WO2003062236.

Several process for preparation of palbociclib were described for example in WO2016016769 by Sun, WO2016030439 by Ratiopharm or in Org. Process Dev. 2016, 20, 1191-1202, Org. Process Dev. 2016, 20, 1203-1216, Org. Process Dev. 2016, 20, 1217-1226.

The procedure described in Org. Process Dev. articles is depicted in following scheme:

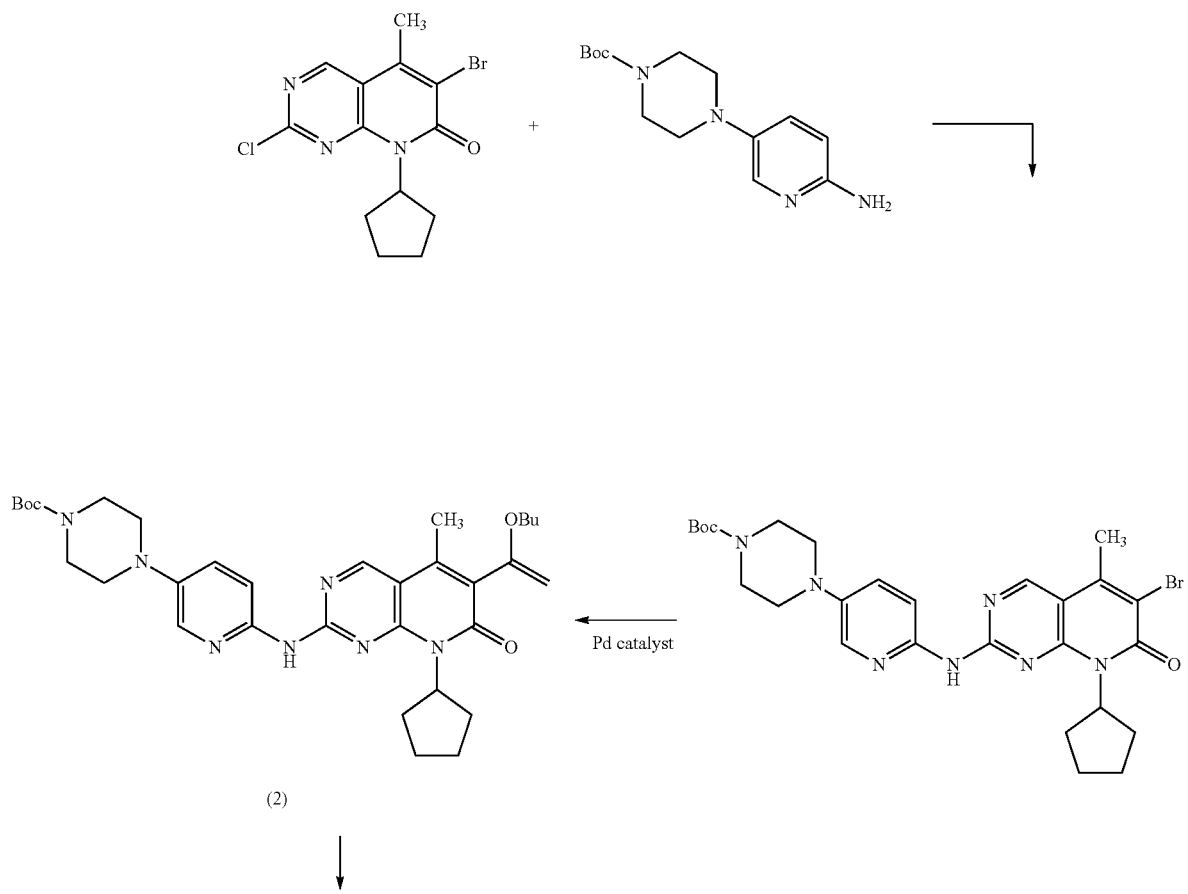

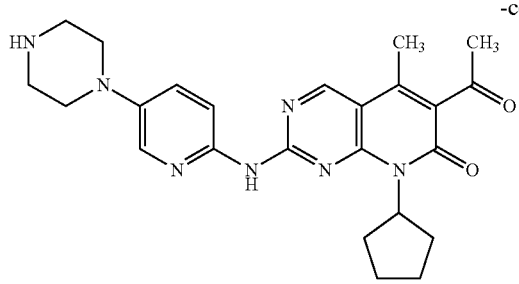

Palladium, used in the reaction step for preparation of compound (2) as a catalyst, should be removed either from compound of formula (2) or from final palbociclib. Removal of palladium is not trivial because the required palladium levels in final palbociclib are low.

Thus, there is still a need to find an improved process for preparation of palbociclib which would provide final API with low levels of both palladium and other impurities.

BRIEF DESCRIPTION OF THE PRESENT INVENTION

The present invention relates to a process for preparation of compound of formula (1) or a salt thereof,

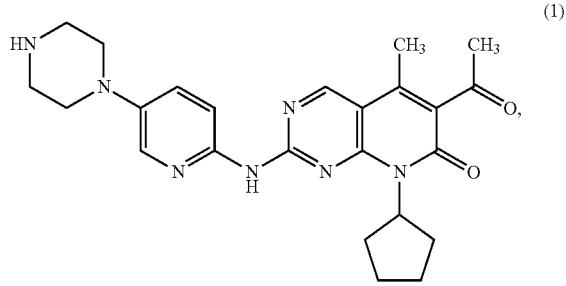 [SMILES: CC(=O)c1c(C)c2cnc(Nc3ccc(N4CCNCC4)cn3)nc2n(C2CCCC2)c1=O]

(1)

the process comprising:
a. Reacting compound of formula (3) and compound of formula (4) to provide compound of formula (2),

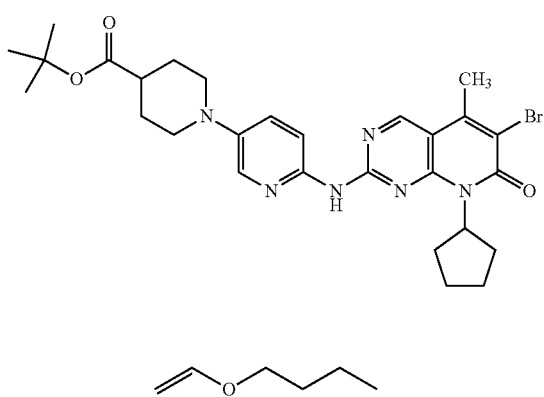

(3)

(4)

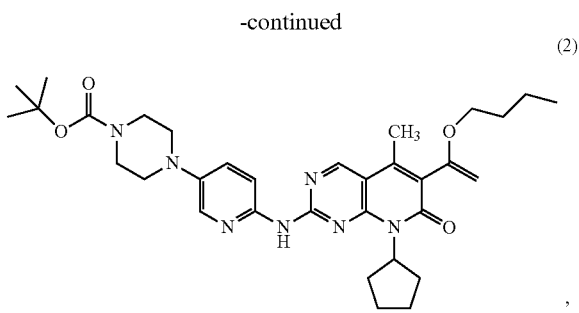

(2)

in a solvent mixture comprising methanol and butanol;
b. Adding water;
c. Isolating solid crystalline form of compound (2) characterized by XRPD pattern having 2θ values 5.5°, 7.5°, 9.7°, 10.1°, 14.5°, 15.9°, 18.1°, 20.2° and 21.5° degrees 2 theta (±0.2 degrees 2 theta);
d. Transforming compound of formula (2) into compound of formula (1).

In a second aspect the invention relates to the solid crystalline form of compound (2) used for the preparation of compound 1, characterized by XRPD pattern having 2θ values 5.5°, 7.5°, 9.7°, 10.1°, 14.5°, 15.9°, 18.1°, 20.2° and 21.5° degrees 2 theta (+0.2 degrees 2 theta.

BRIEF DESCRIPTION OF THE DRAWINGS

The sole FIGURE is an XRPD pattern of compound of formula (2) prepared according to Example 1 or Example 2 or Example 3.

DETAILED DESCRIPTION OF THE INVENTION

The present invention relates to a process for preparation of compound of formula (1) or a salt thereof,

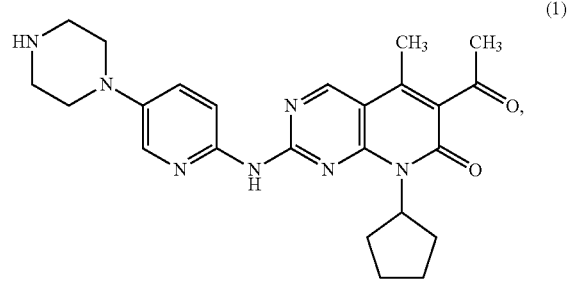 [SMILES: CC(=O)c1c(C)c2cnc(Nc3ccc(N4CCNCC4)cn3)nc2n(C2CCCC2)c1=O]

(1)

the process comprising:
a. Reacting compound of formula (3) and compound of formula (4) to provide compound of formula (2), (3)

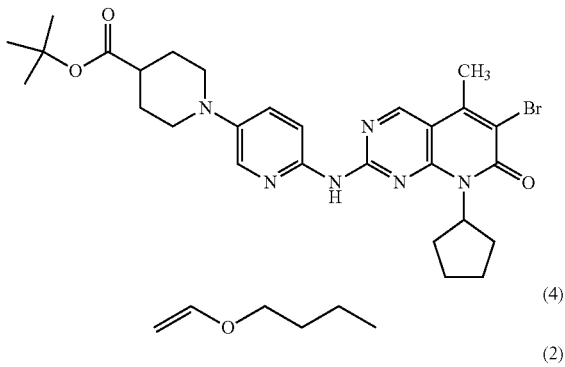

(4)

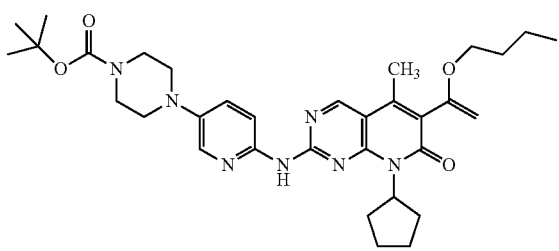

(2)

in a solvent mixture comprising methanol and butanol;
b. Adding water;
c. Isolating solid crystalline form of compound (2) characterized by XRPD pattern having 2θ values 5.5°, 7.5°, 9.7°, 10.1°, 14.5°, 15.9°, 18.1°, 20.2° and 21.5° degrees 2 theta (±0.2 degrees 2 theta);
d. Transforming compound of formula (2) into compound of formula (1).

Compounds (3) and (4) are either commercially available or can be prepared by processes known in the prior art, for example described in Org. Process Dev. 2016, 20, 1191-1202, Org. Process Dev. 2016, 20, 1203-1216, Org. Process Dev. 2016, 20, 1217-1226.

Prior art describes the reaction step a. done in sole butanol as a reaction solvent. We have surprisingly found that use of mixture of methanol and butanol, preferably a mixture comprising 30 to 99% (wt) of methanol, more preferably 30 to 65%, even more preferably 50-65% of methanol, allows both decrease of reaction temperature and decrease in reaction times. That result in a more economical process which is suitable for higher scales and in a decrease of impurities formed in the course of reaction.

In the beginning of the reaction the reaction mixture is a suspension because compound (3) is poorly soluble in the used solvent mixture. When the mixture of methanol and butanol comprises between 30-65% of methanol, preferably between 50 and 65% of methanol, the reaction mixture is a suspension in the beginning, during the course of the reaction it becomes a solution, because compound of formula (2) is soluble in the solvent mixture and the reaction mixture can be optionally filtered after the reaction is finished. When the solvent mixture comprises more than 65% of methanol it remains suspension, because compound (2) is not soluble in this solvent mixture.

The molar ratio between compound (3) and compound (4) is preferably between 1:2 and 1:6, even more preferably it is between 1:2.5 and 1:3.5. The concentration of compound (3) in the mixture of methanol and butanol is preferably between 0.5 g/g and 3 g/g, more preferably it is between 0.8 g/g and 1.5 g/g.

The reaction between compounds (3) and (4) is performed in the presence of Pd catalyst, for example Pd/C, Pd(OAc)2 or [1,1'-bis(diphenylphosphino)ferrocene]dichloropalladium (II). The reaction can be optionally performed in the presence of a phosphine, for example bis-[2-(diphenylphoshpino)phenyl]ether (DPEPhos).

The molar ratio of used Pd catalyst and compound of formula (3) is preferably between 1:30 and 1:45, more preferably between 1:35 and 1:41. The molar ratio between Pd catalyst and the phosphine is preferably between 1:1 and 1:1.5, more preferably it is 1:1.2.

The reaction between compounds (3) and (4) is preferably performed at a temperature between 45 and 75° C., more preferably at a temperature between 55 and 65° C., even more preferably between 60° C. and 63° C. for 2 to 7 hours preferably for 3 to 5 hours.

The reaction progress can be monitored by any suitable analytical method for example by HPLC or GC.

When the reaction is finished, methanol can be added to the mixture so that the mixture at the end of methanol addition comprises 70-99% (wt) of methanol. To the mixture water is added (step b.). The ratio (wt:wt) between water and the solvent mixture of butanol and methanol is preferably between 1:2.5 and 1:6, more preferably between 1:3 and 1:5. Water is preferably added for a time period between 20 and 120 minutes. The mixture is cooled preferably to a temperature between −10° C. and 10° C., more preferably to a temperature between 0° C. and 5° C. and stirred at this temperature for 30 to 240 minutes, preferably for 60 minutes to precipitate compound of formula (2) from the mixture. Obtained solid form of compound of formula (2) is isolated (step c.) from the mixture by any suitable technique, for example by filtration. Isolated solid form of compound of formula (2) is characterized by XRPD pattern having 2θ values 5.5°, 7.5°, 9.7°, 10.1°, 14.5°, 15.9°, 18.1°, 20.2° and 21.5° degrees 2 theta (+0.2 degrees 2 theta). The solid form can be further characterized by XRPD pattern having 2θ values 5.5°, 7.5°, 9.7°, 10.1°, 11.6°, 14.5°, 15.0°, 15.4°, 15.9°, 17.0°, 18.1°, 18.7°, 20.2° and 21.5° degrees 2 theta (±0.2 degrees 2 theta). The solid form can be also characterized by a XRPD spectrum depicted in the sole FIGURE.

Org. Process Dev. 2016, 20, 1203-1216 describes three solid forms of compound (2), Forms A, B and C. The solid form of compound (2) prepared according to the presented invention not only shows a good crystallinity and stability but also a better purity with respect to the content of palladium in comparison with the Forms A, B or C prepared according to the prior art. Process Dev. 2016, 20, 1203-1216 discloses that prepared solid forms of compound of formula (2) contain 500 ppm of palladium, the content thereof can be further decreased to 200 ppm by using of 1,2-diaminopropane. Solid form of compound of formula (2) prepared according to the presented invention comprises typically 10-40 ppm of palladium, the content thereof can be decreased to 3-5 ppm by using of 1,2-diaminopropane.

The compound of formula (2) can be further recrystallized by a process comprising:
  i. Mixing the solid form of compound (2) with a mixture comprising methanol and tetrahydrofuran;
  ii. Heating the mixture;
  iii. Adding water;
  iv. Isolating a solid form of compound of formula (2).

The ratio (wt:wt) between methanol and tetrahydrofurane in step i. is preferably between 3:1 and 18:1, more preferably it is between 4.5:1 and 5.5:1, and even more preferred ratio is 5.2:1. The concentration of compound (2) in the solvent mixture can be between 0.03 g/ml and 0.09 g/ml. The mixture is heated (step ii.) to a temperature preferably between 40° C. and 75° C., more preferably between 50° C. and 60° C. to dissolve the compound of formula (2). The mixture is stirred at this temperature preferably for between 5 and 300 minutes. To the mixture water is added (step iii.). The ratio water:mixture of methanol and tetrahydrofurane (wt:wt) is preferably between 1:2.5 and 1:7, more preferably between 1:3 and 1:4. The mixture can be cooled to a temperature between −10° C. and 25° C. Solid form of compound of formula (2) can be isolated (step iv.) by any suitable technique, for example by filtration.

The isolated solid form of compound of formula (2) is characterized by XRPD pattern having 2θ values 5.5°, 7.5°, 9.7°, 10.1°, 14.5°, 15.9°, 18.1°, 20.2° and 21.5° degrees 2 theta (±0.2 degrees 2 theta). The solid form can be further characterized by XRPD pattern having 2θ values 5.5°, 7.5°, 9.7°, 10.1°, 11.6°, 14.5°, 15.0°, 15.4°, 15.9°, 17.0°, 18.1°, 18.7°, 20.2° and 21.5° degrees 2 theta (±0.2 degrees 2 theta). The solid form can be also characterized by a XRPD spectrum depicted in the sole FIGURE.

The compound of formula (2) is further transformed into compound of formula (1) by processes known in the prior art. For example, compound of formula (2) is mixed with an acid in a solvent or a solvent mixture. Suitable acids are for example hydrochloric acid, nitric acid, phosphoric acid, sulfuric acid, hydrobromic acid, hydroiodic acid, acetic acid, oxalic acid, valeric acid, oleic acid, palmitic acid, stearic acid, lauric acid, boric acid, benzoic acid, lactic acid, benzenesulfonic acid, citric acid, maleic acid, fumaric acid, succinic acid, tartaric acid, naphthalene dicarboxylic acid, methanesulfonic acid, lactic acid, lauryl sulfuric acid, isethionic acid. The molar ratio between compound of formula (2) and the acid can be between 1:2 and 1:8, preferably it is between 1:4 and 1:6. Suitable solvents are for example ketones, esters, ethers, amides, nitriles or organic acids, alcohols, aliphatic and aromatic hydrocarbons, chlorinated hydrocarbons, water or their mixtures. Aliphatic $C_1$-$C_4$ alcohols, esters or their mixtures are preferred. The most commonly used solvents are methanol, ethanol, water or their mixtures. The concentration of compound of formula (2) in the solvent can be between 0.08 g/ml and 0.20 g/ml, preferably it is between 0.1 g/ml and 0.15 g/ml.

The reaction mixture can be heated to a temperature between 40° C. and the reflux temperature of used solvent(s) and stirred at this temperature for 1 to 10 hours. The reaction progress can be monitored by any suitable analytical method for example by HPLC or GC.

The mixture can be cooled to a temperature between −10° C. and the room temperature.

A solid form of a salt of compound of formula (1) with the suitable acid can be optionally isolated by for example by filtration.

Compound of formula (1) is obtained from a salt of compound of formula (1) by contacting a solution of the salt with a base (for example NaOH, KOH, NaHCO$_3$, Na$_2$CO$_3$, K$_2$CO$_3$, KHCO$_3$) in a suitable solvent (for example a mixture of $C_1$-$C_4$ alcohol and water). The final pH of the mixture should be higher that 8, preferably it is between 10-11.

Obtained solid form of compound of formula (1) can be isolated by any suitable technique, for example by filtration.

Obtained solid form of compound of formula (1) (palbociclib) preferably has the surface area between 6-16 m²/g, more preferably between 7-14 m²/g and is preferably in polymorph form A disclosed in WO2014128588. Obtained solid compound of formula (1) comprises less than 30 ppm of palladium, preferably less than 10 ppm of palladium.

The invention will be further described with reference to the following non-limiting examples.

EXAMPLES

XRPD spectrum was obtained using the following measurement conditions:

Panalytical Empyrean diffractometer with Θ/2Θ geometry (transmission mode), equipped with a PixCell 3D detector;

| | |
|---|---|
| Start angle (2θ): | 2.0° |
| End angle (2θ): | 35.0° |
| Step size: | 0.026° |
| Scan speed: | 0.0955°/seconds |
| Radiation type: | Cu |
| Radiation wavelengths: | 1.5406 Å (Kα1), primary monochromator used |
| Divergence slit: | ½° |
| Antiscatter slit: | ½° |
| Soller slit: | 0.02 rad |
| Detector slit: | 7.5 mm |
| Rotation speed: | 30 rpm |

The specific surface area (SSA) is assessed with a Quantachrome NOVA touch 2LX. The N$_2$ is used as measuring gas and BET method is used to evaluate SSA. The following setup has been used for the measurement:

Adsorbate: Nitrogen

Sample cell: 9 mm large bulb cell, long; Measurement is performed with the corresponding filler rod Sample masses*: approximately ¾ of cell bulb Degassing conditions: 960 min at 30° C. under vacuum (ramping 10° C./min)

Measured points of isotherm: 11 equidistant points in the range 0.05-0.30 p/p$_0$ **

Points analyzed using BET: 7 equidistant points from whole range 0.05-0.20 p/p$_0$ Use data reduction adsorbate model: Yes (N$_2$)

Bath thermal delay: at least 600 s

P$_0$ Option: continuous (measured each 30 minutes)

Void volume mode: Helium measure

Equilibration time: 160 s

Equilibration timeout: 2400 s

Tolerance: 0.05

* Used amount of sample depends on its SSA and other physical parameters. The real surface area of sample in measuring cell should be between 1 m²/g and 20 m²/g.

** Points above or below this range can be measured.

Example 1

Preparation of a Solid Form of Compound of Formula (2)

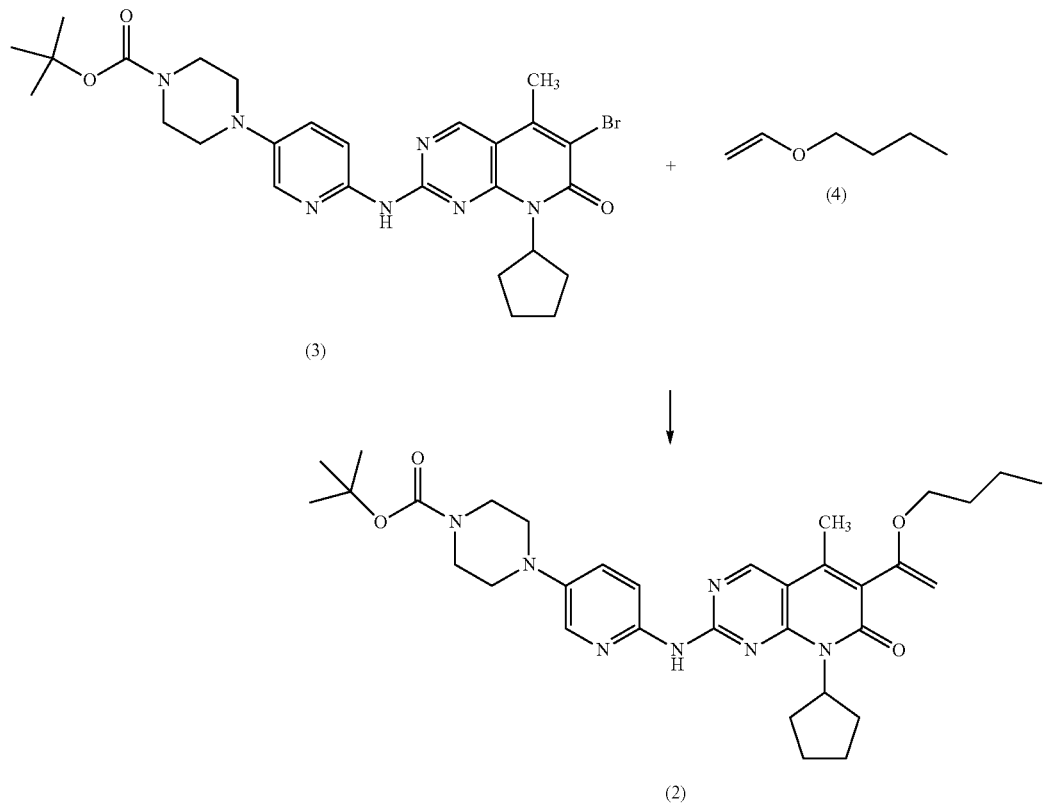

100 g of compound of formula (3) was suspended in 375 g of dry 1-butanol and 625 g of dry methanol at 40° C. The suspension was placed under nitrogen and 50 g of compound of formula (4), 50 g of diisopropylethylamine, 1 g of Pd(OAc)2 and 3 g of DPEPhos were added. The reaction mixture was heated at 60° C. and stirred at this temperature for 3 hours. The mixture was filtered, to the filtrate 250 g of methanol and 300 g of water during 40 minutes were added. The suspension was cooled to 0-5° C., solid compound (2) was filtered off and washed with a mixture of 240 g of methanol and 40 g of water. The filter cake was dried at 65° C. 94 g of compound of formula (2) was obtained (yield 90% of the theoretical yield) in HPLC purity 99.1%. XRPD pattern of the obtained solid corresponds to XRPD pattern depicted in the sole FIGURE. The content of palladium in obtained solid was 25 ppm.

Example 2

Preparation of a Solid Form of Compound of Formula (2)

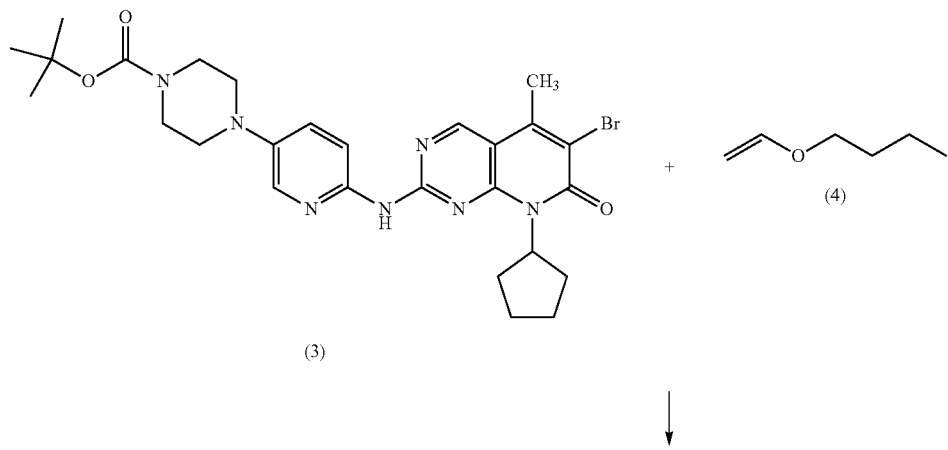

-continued

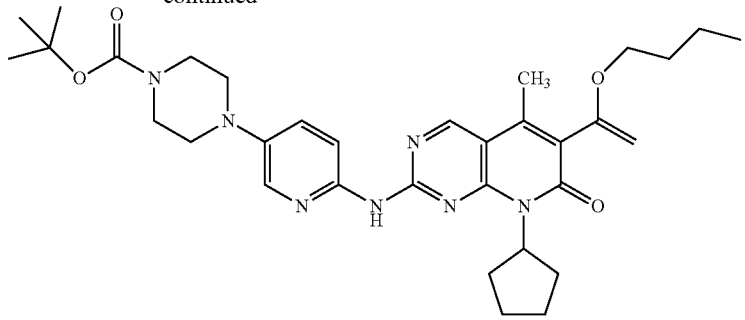

(2)

2 g of compound of formula (3) was suspended in 3.75 g of dry 1-butanol and 75 g of dry methanol at 40° C. The suspension was placed under nitrogen and 1.2 g of compound of formula (4), 1.2 g of diisopropylethylamine, 0.0625 g of Pd(OAc)2 and 0.1875 g of DPEPhos were added. The reaction mixture was heated at 55° C. and stirred at this temperature for 3 hours. The mixture was filtered, to the filtrate 36 g of water during 15 minutes were added. The suspension was cooled to 0-5° C., solid compound (2) was filtered off and washed with a mixture of 29 g of methanol and 5 g of water. The filter cake was dried at 65° C. 1.81 g of compound of formula (2) was obtained (yield 88% of the theoretical yield) in HPLC purity 98.9%. XRPD pattern of the obtained solid corresponds to XRPD pattern depicted in the sole FIGURE. The content of palladium in obtained solid was 28 ppm.

Example 3

Recrystallization of Compound of Formula (2)

5 g of compound of formula (2) prepared according to Example 1 were suspended in 75 g of methanol and 3 g of tetrahydrofuran. The suspension was heated to 55° C. to dissolve the compound of formula (2). To the mixture 25 g of water were added during 10 minutes. The suspension was cooled to 0-5° C. and stirred at this temperature for 10 minutes. The mixture was filtered off, the filter cake was washed with a mixture of 12 g of methanol and 2 g of water. 4.7 g of compound of formula (2) (94.6% of the theoretical yield) was obtained. XRPD pattern of the obtained solid corresponds to XRPD pattern depicted in the sole FIGURE. The content of palladium in obtained solid was 13 ppm.

Example 4

Process for Preparation of Compound of Formula (1)

100 g of compound of formula (2) prepared according to Example 3 was suspended in 790 g of methanol. Into the suspension 115 g of 26.2% solution of HCl in ethanol was added during 10 minutes. The mixture was heated at 55-57° C. and was stirred at this temperature for 2 hours. The suspension was cooled to 0-5° C. and filtered off. The cake was washed with 200 g of methanol. Filtrated solid was dissolved in a mixture of 400 g methanol and 500 g of water. The mixture was heated to 40° C. To the mixture 15.4 g of NaOH in 155 g of water was added during 60 minutes to set the pH of the mixture to 10-11. The suspension was stirred for 60 minutes, cooled to 25° C. and filtered. Then filtration cake was washed with 2×500 g of water and 157 g of acetone. The cake was dried to provide 69 g of compound of formula (1) with HPLC purity 99.9% (HPLC IN). The specific surface area of obtained compound of formula (1) was 9.5 m²/g and the content of palladium in the obtained solid was 10 ppm.

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

The invention claimed is:

1. A process for preparation of a compound of formula (1) or a salt thereof, (1)

[structure of formula (1)]

the process comprising:
(a) reacting in a solvent mixture comprising methanol and butanol, a compound of formula (3) and a compound of formula (4) to provide a compound of formula (2),

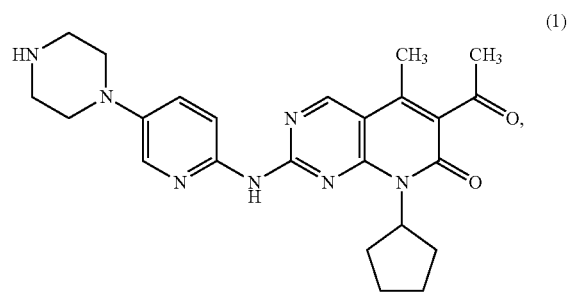 [SMILES: CC(=O)c1c(C)c2cnc(Nc3ccc(N4CCNCC4)cn3)nc2n(C2CCCC2)c1=O]

(3)

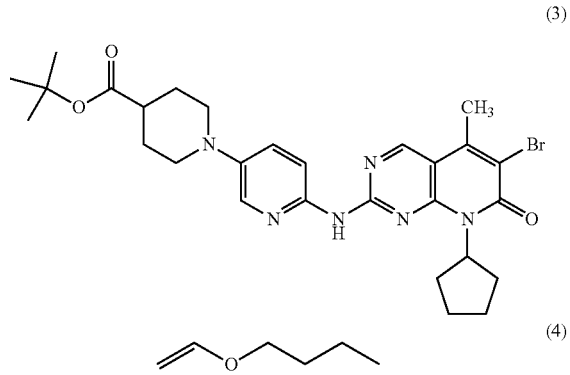

(4)

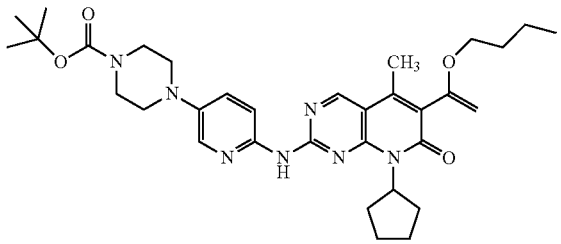

and (b) transforming the compound of formula (2) into the compound of formula (1) or a salt thereof.

2. The process according to claim 1, wherein the solvent mixture comprises 30-99% (wt) of methanol.

3. The process according to claim 2, wherein the mixture comprises 30-65% of methanol.

4. The process according to claim 3, wherein the mixture comprises 50-65% of methanol.

5. The process according to claim 1, wherein the reaction temperature in step (a) is between 55° C. and 65° C.

6. The process according to claim 4, wherein the reaction temperature in step (a) is between 55° C. and 65° C.

7. The process according to claim 1, further comprising isolating a solid form of the compound of formula (2).

8. The process according to claim 7, wherein the solid form of the compound of formula (2) is characterized by XRPD pattern having 2θ values 5.5°, 7.5°, 9.7°, 10.1°, 14.5°, 15.9°, 18.1°, 20.2° and 21.5° degrees 2 theta (+0.2 degrees 2 theta).

9. The process according to claim 1, which further comprises isolating a solid form of the compound of formula (1).

10. The process according to claim 9, wherein the isolated form of the compound of formula (1) has a specific surface area between 6 and 16 m²/g.

11. The process according to claim 9, wherein the isolated compound of formula (1) comprises less than 30 ppm of palladium.

* * * * *